| United States Patent [19] | [11] Patent Number: 4,761,376 |
| Kulpa et al. | [45] Date of Patent: Aug. 2, 1988 |

[54] FACULTATIVELY ANAEROBIC MICROORGANISM FOR DEGRADING TOXIC WASTE MATERIALS

[75] Inventors: Charles F. Kulpa, South Bend, Ind.; Stanley A. Sojka, Buffalo, N.Y.

[73] Assignee: Occidental Chemical Corporation, Niagara Falls, N.Y.

[21] Appl. No.: 881,770

[22] Filed: Jul. 3, 1986

[51] Int. Cl.[4] .............................................. C02F 3/34
[52] U.S. Cl. .................................. 435/262; 435/264; 435/266
[58] Field of Search ........................ 435/262, 264, 266

[56] References Cited

U.S. PATENT DOCUMENTS 4,477,570  10/1984  Colaruotolo et al. .............. 435/253
4,511,657  4/1985  Colaruotolo et al. .............. 435/262

OTHER PUBLICATIONS

Shintaku et al.–Chem. Abst. vol. 94 (1981), p. 142,294p.
Hakulinen et al.–Chem. Abst. vol. 103 (1985), p. 26,622z.

Primary Examiner—Sam Rosen
Attorney, Agent, or Firm—James F. Tao; William G. Gosz

[57] ABSTRACT

A facultatively anaerobic microorganism of a strain of *Klebsiella oxytoca* is disclosed for degrading toxic waste materials into more environmentally acceptable materials. Processes for utilizing the microorganism in a sequencing batch reactor, and for treating industrial and municipal wastes, such as chemical waste landfill leachate and chemical process wastewater, are also disclosed.

10 Claims, No Drawings

FACULTATIVELY ANAEROBIC MICROORGANISM FOR DEGRADING TOXIC WASTE MATERIALS

BACKGROUND OF THE INVENTION

This invention relates to a new facultatively anaerobic microorganism for degrading recalcitrant toxic waste materials, and particularly chlorinated aromatic compounds, into materials which are more environmentally acceptable.

The chemical industry annually generates enormous quantities of synthetic chemicals such as dielectric fluids, flame retardants, refrigerants, heat transfer fluids, lubricants, protective coatings, pesticides, including herbicides and insecticides, as well as many other chemicals and petroleum products used in agriculture, industry and health care. While these materials are invaluable and sustain a high standard of living for the population, they are foreign to the biosphere and can cause serious problems when released into the environment. Other sources of toxic chemicals include the waste materials generated during the manufacture of such useful chemicals.

Large amounts of the toxic chemicals generated annually by the chemical industry accumulate in animal and plant tissues and can cause serious health problems. Since these chemicals are not products of natural processes, and may possess structural features which are not commonly found in nature, they tend to persist in the environment and are resistant to degradation from naturally occuring organisms. Halogenated aromatic compounds are known to be particularly hazardous and also strongly resistant to biodegradation due to their cyclic nature and low concentration in the environment. Therefore, they tend to persist and accumulate to dangerous levels. Some of these materials are toxic, mutagenic and/or carcinogenic at very low concentrations. Polychlorinated biphenols (PCB's), chlorinated phenoxyacetates, and chlorinated benzoic acids (CBA's) are examples of chlorinated aromatic compounds considered to be hazardous wastes and priority pollutants. These chemicals are introduced directly into the biosphere as herbicides, pesticides, electrical transformer fluids or land treatment systems, or indirectly from unsuccessful landfills, chemical spills, or as wastes from chemical manufacturing processes, depending on their production method, shipment, use and disposal. Human exposure to and concern over these chemicals has increased in recent years due to increasing population density and industrial activity. Chlorinated benzoic acids or chlorobenzoates are of particular concern since they are intermediates in the microbial metabolism of more complex chlorinated aromatic compounds.

A variety of microorganisms have been isolated that have the capability of efficiently utilizing aromatic organic chemicals as sole carbon sources for growth (e.g. toluene, phenol, and naphthalene). See Clarke, P. H. and Ornston, L. N. (1975) "Metabolic Pathways and Regulations", 1, 191–196 in Clarke, P. H. and Richmond, M. H. (ed.), "Genetics and Biochemistry of Psuedomonas", John Wiley, London. However, the corresponding chlorinated aromatic compounds (chlorotoluenes, chlorophenols, chloronephthalenes) are biodegraded very slowly, if at all. See Alexander, M. (1973) "Non-Biodegradable and Other Recalcitrant Molecules", Biotechnology—Bioengineering, 15: 611–647.

A possible reason for this recalcitrance is the reduced reactivity of halogenated aromatic rings. The aromatic ring must be cleaved for the cycling of carbon in the metabolism of aromatic hydrocarbons. The presence of a halogen substituent on the aromatic ring adversely affects degradation. A halogen is an electronegative substituent which lowers the electron density of sites around the aromatic ring thereby reducing the chemical reactivity of the compound, rendering the ring less susceptible to microbial attack. These steric effects are influenced by the nature, position, and degree of substitution. As the number of halogen substituents increases, the arylhalide becomes less susceptible to microbial attack.

Notwithstanding, microorganisms have been isolated from the environment that are capable of growth on chlorinated aromatic compounds. For example, Chakrabarty, A. M., (1976) "Plasmids in Pseudomonas"; Ann. Rev. Genet. 10, 7–30, discloses bacteria which utilize haloaromatic compounds and the degradative pathways of intermediates involved. Several other publications deal with the microbiodegradation of halogenated hydrocarbons. For example, Bourquin, A. W. and Gibson, D. T. (1978) "Microbial Degradation of Halogenated Hydrocarbons; Water Chlorination Environmental Impact and Health Effects", 2, 253–264 disclose various microorganisms such as Aspergillus sp., Achromobacter sp., Arthrobacter sp. and Clostridium sp., as useful for dehalogenation of various substrates such as 2-chlorophenoxyacetate, 2,4-dichlorophenol, 3-chlorobenzoate, hexachlorocyclohexane, and 4-chlorobenzoate. Gibson, D. T., Koch, J. R., Schuld, C. L. and Kallio, R. E. (1968)—Biochemistry, 7 No. 11 3795–3802 in their paper on "Oxidative Degradation of Aromatic Hydrocarbons by Microorganisms including the Metabolism of Halogenated Aromatic Hydrocarbons," disclosed Pseudomonas putida as useful in the degradation of toluene and chlorinated compounds such as halobenzenes and p-chlorotoluene and state that the presence of halogen atoms greatly reduces the biodegradability of aromatic compounds. They also disclose that microorganisms have been isolated that have the capability to cometabolize a chlorinated aromatic chemical during growth on its nonchlorinated analog. For example, the conversion of chlorotoluene to chlorocatechol during growth of Pseudomonas putida on toluene has been demonstrated. This organism would not further metabolize the chlorocatechol, rather it is known that other microorganisms possess the ability to metabolize chlorocatechols. See Dorn, E. M., Hellwig and Reineke, W. and Knackmuss, H. J. (1974), "Isolation and Characterization of a 3-Chlorobenzoate Degrading Pseudomonas", Arch. Microbiology 99, 61–70 and also see Evans, W. C.; Smith, B. S. W.; Fernley, H. N.; and Davies, J. I, (1971), "Bacterial Metabolism of 2,4-Dichlorophenoxy Acetate", Biochem J., 122, 543–55. Chlorocatechol is known to be an intermediate in many of the metabolic pathways for utilization of chlorinated aromatic compounds. The chlorocatechol is further metabolized with the subsequent removal of chlorine. See Tiedje, J. M.; Duxbury, J. J.; Alexander, M. and Dawson, J. E. (1969), 2,4 D Co-metabolism: Pathway of Degradation of Chlorocatechols by Arthrobacter, J. Agr. Food Chem, 17, 1021–2026. Hartmann, J., Reineke, W., Knackmuss, H. J., (1979) Applied & Environmental Microbiology; 37, No. 3, 421–428 show a species of Pseudomonas identified as sp. WR 912 capable of degrading chlorobenzoic acids. Shubert, R., (1979) Fed. Ministry for Research and Technology, Goethe University, Frankfurt, W. Germany in his paper on "Toxicity of Organohalogen Compounds", discloses the minimal inhibitory concentrations preventing growth of various bacteria including a *Pseudomonas cepacia* in various chlorinated compounds including chlorotoluene.

Cometabolism is effective in the biodegradation of haloaromatic xenobiotic compounds because they do not have to serve as a sole source of carbon and energy for the microorganisms. It allows a microbial population to eliminate the toxicity of a hazardous compound while growing on another. In addition, through a series of cometabolic reactions among different microorganisms, total degradation of a compound could occur. PCB's, chlorinated phenoxyherbicides, and chlorinated benzoic acids are all known to be degraded slowly through cometabolism.

The cometabolic theory was utilized to develop a technique termed analogue enrichment as a means of inducing microbial degradation of environmental pollutants. See Horvath, R. S. and Alexander, M. "Cometabolism of m-Chlorobenzoate by an Arthrobacter", *Applied Microbiology* 20, 254 (1970). This technique takes into account the fact that microorganisms will attack a normally non-biodegradable substance in the presence of a substrate which is similar in structure to the target compound. The analogue induces the necessary enzyme system for the degradation of the recalcitrant compound. Analogue enrichment increases the decomposition rate of the target compound.

It has been suggested that because halogenated compounds are not generally found in nature, microorganisms have not evolved which possess efficient enzyme systems or genes which express themselves for the degradation of such chemicals; see Chatterjee, D. K., Kellogg, S. T., Furukawa, K., Kilbane, J. J., Chakrabarty, A. M., "Genetic Approaches to the Problems of Toxic Chemical Pollution", Third Cleveland Symposium on Macromolecules, 1981. Chakrabarty disclosed a technique for artificially inducing the biodegradability of 2,4,5 trichlorophenyl acetic acid (2,4,5 T) by gradually exposing bacteria to increased concentrations of the chemical over the course of about one year; see Chatterjee, D. K., Kellog, S. T., Eatkins, D. R. and Chakrabarty, A. M. in "Molecular Biology, Pathogenicity and Ecology of Bacterial Plasmids", Plenum Publishing Corp., N. Y., 1981, pp. 519–528.

U.S. Pat. Nos. 4,477,570 and 4,493,895, issued Oct. 16, 1984 and Jan. 15, 1985, respectively, the disclosures of which are incorporated by reference herein, disclose strains of *Pseudomonas cepacia* which are aerobic microorganisms and possess the capability of biodegrading halogenated organic compounds such as chlorobenzoates and chlorotoluates. These microorganisms were isolated from soil samples obtained from a landfill site which had been used for the disposal of chlorinated organic wastes during the period 1955–1975, and are identified as ATCC 31939, ATCC 31940, ATCC 31941, ATCC 31942, ATCC 31943, ATCC 31944, and ATCC 31945, all based on deposits made at the American Type Culture Collection. The plasmids contained in these microorganisms which code for the degradation of chlorinated aromatic compounds were isolated and designated as pRO 4.7, pRO 31 and pRO 54. Other plasmids which code for the degradation of chlorinated aromatic compounds are shown in the following Table 1:

TABLE 1

| Plasmid | Degradative Pathway |
| --- | --- |
| pAC21 | p-chlorobiphenyl |
| pAC25 | 3-chlorobenzoate |
| pAC27 | 3- and 4-chlorobenzoate |
| pAC29 | 3-, 4-, and 3,5-dichlorobenzoate |
| pJR2 | 2,4-dichlorophenoxyacetate |
| pAC31 | 3,5-dichlorobenzoate |
| pKF1 | chlorinated biphenyls |
| pJP1 | 2,4-dichlorophenoxyacetate |

The plasmids listed in Table I are found in such diverse microorganisms as *Pseudomonas putida*, *Pseudomonas aeruginosa*, *Klebsiella pneumonia*, *Serratia manscescens*, gram negative Acinetobacter and gram positive Arthrobacter.

*Klebsiella pneumonia* and *Serratia marescens* are facultatively anaerobic enteric bacteria which were isolated from PCB-contaminated sediment of the Hudsom River. These microorganisms harbor the pAC21 plasmid and are capable of metabolizing p-chlorobiphenyl as their sole source of carbon and energy. See Kamp, P. V. and Chakrabarty, A. M., "Plasmids Specifying p-Chlorobiphenyl Degradation in Enteric Bacteria", in *Plasmids of Medical, Environmental, and Commercial Importance*, Biomedical Press, Elsevier, North-Holland (1979).

Enteric bacteria are not known for their ability to utilize hydrocarbons since they do not express genes for hydrocarbon degradation in the laboratory. However, the Hudson River isolates catabolize p-chlorobiphenyl as well as 4-chlorobenzoic acid, p-hydroxybenzoate and 2,4-D. The pAC21 plasmid is believed to be responsible for this activity. Strong selective pressures including high, localized concentrations of a toxic substance and the river bottom environment favored the appearance of such novel microorganisms.

The use of microorganisms for the treatment of wastewater is an economical alternative to physical treatment systems since biological treatment involves lower capital investment, lower energy requirements, a self-sustaining operation, and finally, the possibility for product recovery. In addition, biological systems offer the possibility of treatment in pre-existing municipal waste facilities, thus lowering the initial capital investment even further.

One particular biological treatment system of current interest is the sequencing batch reactor (SBR), which is a fill and draw activated sludge system operated in a batch treatment mode and utilizing a single tank for equalization, aeration and sedimentation. The use of a sequencing batch reactor with an inoculum of microorganisms capable of degrading chlorinated hydrocarbons is described in U.S. Pat. No. 4,511,657, issued Apr. 16, 1985, the disclosure of which is incorporated by reference herein.

Although several types of microorganisms which demonstrate the capacity to use chlorinated aromatic compounds as their sole source of carbon and energy are known, most of these are aerobic microorganisms which require oxygen for growth. Consequently, these bacteria would not be suitable for use in oxygen lean environments such as subsoil environments and underwater sediments which can contain toxic chemicals or wastes resulting from spills or direct applications to the soil. A facultatively anaerobic microorganism which could survive with or without oxygen by shifting to different metabolic processes in each case and which has the capability of degrading haloaromatic compounds would be extremely useful for soil detoxification.

SUMMARY OF THE INVENTION

In accordance with the present invention, a novel facultatively anaerobic microorganism designated as *Klebsiella oxytoca* strain SAL-18A has been discovered having the capacity to utilize mono- and di-chlorobenzoates as its sole source of carbon and energy in solid medium. This microorganism was discovered in leachate samples obtained from a landfill site which had been used for the disposal of chlorinated organic wastes. Processes for utilizing this microorganism to degrade halogenated organic chemicals contained in soils and leachate are also disclosed.

DETAILED DESCRIPTION OF THE INVENTION

A new microorganism has been isolated from leachate obtained from a chemical waste landfill site which had been used for the disposal of chlorinated organic wastes for a prolonged period of time. The new microorganism is identified as *Klebsiella oxytoca* strain SAL-18A having accession number IVI-10113, based on a deposit at In Vitro International, Inc. It is a gram negative, facultative anaerobic coccobacilli, and is able to grow on a mixed feed of non-haloaromatics and haloaromatics, and on the raw leachate itself. Procedures for isolation, separation and purification of this microorganism are well known and are more fully described in U.S. Pat. No. 4,477,570.

This microorganism has the unique characteristic of being able to grow both aerobically and anaerobically. This characteristic could enable the microorganism to be used in the treatment of soils where the toxic materials have penetrated to subsoil environments which lack oxygen to foster bacterial growth. For example, there are known landfills in which the stored chemicals are found 50 feet or more below the surface. In addition, depending on location, landfills can experience extremes of temperature ranging from 100° F. in the summer to −30° F. in the winter. A microorganism which is potentially useful for soil detoxification must be capable of surviving at such depths and under these extreme environmental conditions.

Methods for applying the bacteria to the sites of the contamination are well known in the art. Such methods are described in U.S. Pat. No. 4,477,570. For example, a suitable inoculum containing the microorganism can be injected along with nutrient media to a predetermined depth into the soil. Once established, the organism can utilize the waste stored in the landfill as its sole source of carbon and energy, thereby detoxifying the landfill.

The microorganism of the present invention can also be used in a sequencing batch reactor as part of the stable biomass of the reactor to degrade haloaromatic compounds present in the reactor feed stream. In this manner, the sequencing batch reactor can be advantageously used to treat chemical landfill leachate containing recalcitrant chlorinated organics under aerobic or anaerobic conditions, such as during an anaerobic phase of the reactor.

A diagram of a typical sequencing batch reactor is provided in R. L. Irvine, *Journal of Water Pollution Control Federation*, Vol. 51, No. 2, pages 235–304 (1979).

As contemplated herein, the sequencing batch reactor contains an activated sludge inoculated with the microorganism of this invention. The type of activated sludge employed is not critical, and any municipal or industrial sludge may be used since it generally contains a variety of organisms capable of metabolizing organics. Activated sludge is predominantly composed of bacteria, protozoa, and fungi. Other constituents are often present such as blue-green algae, rotifers, insect larva, etc., but usually not in significant numbers. Over 300 strains of bacteria, 230 species of protozoa and 50 species of fungi have been found in various activated sludges.

The bench scale sequencing batch reactor is made of any material of construction generally employed in wastewater treatment facilities. It is usually cylindrical in shape and is equipped with air diffusers which are used for mixing and aeration. A peristaltic pump is installed in the inlet feed line to the reactor. The reactor is provided with an outlet, and solenoid valves are provided at the outlet and in the air diffuser line. Programmable timers are provided at the pumps and the agitators, if used, or air diffusers, and at the outlet line.

The SBR system may be composed of one or more such vessels, and in biological waste treatment, each tank in the system has five basic operating modes and periods, each of which is named according to its primary function. The periods are FILL, REACT, SETTLE, DRAW and IDLE, in time sequence. FILL (the receiving of raw waste) and DRAW (the discharge of treated effluent) must occur in each complete cycle for a given tank. REACT (the time to complete desired reactions), SETTLE (the time to separate the organisms from the treated effluent), and IDLE (the time after discharging the tank and before refilling) can be eliminated depending on requirements of the treatment problem. For example, if an SBR system were being used for equalization only, each cycle might only involve fill and draw.

The time for a complete cycle is the total time between beginning of fill to end of idle in a single-tank system and between beginning of fill for the first reactor (arbitrarily defined) and the end or idle for the last reactor in a multiple-tank system. In a multiple-tank system, the reactors fill in sequence, the criterion being that one reactor must have completed draw prior to another completing fill.

The present invention will be more particularly described in the following examples. These examples, however, are not intended to limit the scope of the invention except as defined in the appended claims.

EXAMPLE 1— Characterization of Microorganism

The microorganism was kept on LB agar plates with 0.1% (v/v) leachate added to prevent the loss of leachate-degradative activities. LB, per liter of water, consists of 10.0 g. of tryptone, 5.0 gr. of yeast extract. 5.0 g. of sodium chloride, and 1.0 g. of glucose. The pH was adjusted to 7.0 with NaOH. After autoclaving, the leachate was added to 0.1% (v/v). For solid media, agar was added to a concentration of 1.5% (w/v).

Methods of microorganism identification followed standard procedures as outlined in *Bergey's Manual* and the *Journal of General Microbiology*.

An experiment to determine if the microorganism employed the ortho or meta pathway for cleavage of the aromatic ring was performed as outlined in the *Manual of Methods for General Bacteriology*. *Esherichia coli* was used as the negative control.

Growth tests were conducted in 250 ml. Ehrlenmeyer flasks. The inoculant was a turbid solution formed by dispersing approximately one loopful of culture in sterile water. One ml. of inoculant was added to 100 ml. of sterile basal salts medium containing 1.0 mg/ml of the test substrate. Test substrates included 2-chlorobenzoic acid, 3-chlorobenzoic acid, 4-chlorobenzoic acid, and 2,5-dichlorobenzoic acid. Growth on p-hydroxybenzoate was used as a control. After inoculation, the flasks were placed in a 28° C. floor shaker.

Cell density was used as an indication of cell growth. Cell density measurements were taken at 420 nm. using the Bausch and Lomb Spectronic 20.

*Klebsiella oxytoca* strain SAL-18A was isolated from leachate from a chemical waste landfill site. This microorganism, which has been assigned accession number IVI-10113 is a gram negative, facultative anaerobic coccobacilli.

The isolate was tested to determine if it utilized the ortho or meta pathway for cleavage of the aromatic ring, and was found to employ the ortho pathway. The degradation of halogenated aromatic compounds has been shown to occur only via the ortho pathway. The meta pathway is unproductive for the degradation of haloaromatics. Therefore, this microorganism might possess the potential to catabolize haloaromatic compounds.

Growth tests revealed that the isolate was able to utilize p-hydroxybenzoate in the liquid culture as the sole source of carbon and energy. Therefore, the isolate was capable of metabolizing aromatic compounds. However, it was not able to grow in liquid culture on any of the chlorobenzoates as tested here. The presence of the chloride substituent was assumed to be the inhibiting factor suggesting that enzyme systems in this isolate were not capable of attacking the chlorinated aromatic acids.

The fact that this microbe did not grow on the test substrates does not indicate total noninvolvement in the degradation of these compounds. It may have been responsible for partial degradation, or it may only be effective in the degradation of chlorobenzoates via a cometabolic process. Cometabolism has been observed in the degradation of chlorobenzoates. This isolate may therefore require a mixed substrate or mixed culture environment for metabolism of the test compounds.

EXAMPLE 2— Isolation of Plasmids from Microorganism

Prior to plasmid extraction, the microorganism was grown for 20 to 24 hours at 27 degrees Celsium on LB plus 0.1% (v/v) leachate agar plates. The presence of the leachate in the growth medium applied selective pressure on the microorganism for the retention of plasmids.

The plasmid extraction procedure was that of Hanson, J. B. and Olsen, R. H., "Isolation of Large Bacterial Plasmids and Characterization of the P2 Incompatibility Group Plasmids pMG1 and pMG5", *Journal of Bacteriology*, 135, 277 (1978). Stock solutions are listed in Table 2 and plasmid isolation is listed in Table 3.

TABLE 2

| Solution | Contents |
|---|---|
| TE Buffer | 0.5 M tris-(hydroxymethyl)aminomethane (Tris) (pH 8.0) |
| | 0.2 M disodiumethylenediaminetetraacetate (Na2EDTA) (pH 8.0) |
| TES Buffer | 0.05 M Tris |
| | 0.05 M sodium chloride |
| | 5.0 mM Na2EDTA |
| Tris/Sucrose Buffer | 25% (w/v) Sucrose |
| | 0.05 M Tris |
| Na2EDTA Solution | 0.25 M Na2EDTA (pH 8.0) |
| SDS | 20% (w/v) sodium lauryl sulfate in TE |
| Alkaline Denaturation Solution | 3.0 N sodium hydroxide (NaOH) |
| Neutralizing Solution | 2.0 M Tris (pH 7.0) |
| High Salt Solution | 5.0 M sodium chloride (NaCl) |

TABLE 3

| Step | Operation |
|---|---|
| Cell Growth | 20 to 24 hours on LB plus 0.1% (v/v) leachate agar plates |
| Cell Lysis | Washed cells resuspended in 25% Sucrose Buffer with 100 ug. of mutanolysin |
| | Refrigerate in ice bath for one hour |
| | 0.25 M Na2EDTA (pH 8.0) added |
| | SDS added to 4.0% (w/v) |
| | Intermittent heat pulses at 55° C. in water bath |
| Alkaline Denaturation | 3.0 N NaOH added to raise pH to 12.1 to 12.3 |
| Neutralization | 2.0 M Tris (pH 7.0) added to reduce pH to 8.5 to 9.0 |
| Precipitation of membrane-chromosomal complexes | SDS added to 4.0% (w/v) and 5.0 M NaCl added to 1.0 M |
| | Refrigerate in ice bath overnight |
| Concentration of plasmid DNA | Polyethylene glycol added to 10% (w/v) |
| | Refrigerate in ice bath overnight |
| | Centrifugation at 2500 RPM for 5 minutes and resuspend in 0.2 ml. of TES buffer |

Centrifuges used in plasmid isolation included the Fisher Micro-Centrifuge Model 235B for plasmid minipreps. Larger preps were centrifuged in 50.0 ml. propylene centrifuge tubes using the Sorvall Superspeed RC2-B Automatic Refrigerated Centrifuge.

Cesium-chloride equilibrium density gradients of the crude plasmid extracts were performed in the Beckman Nodel 13–50 Ultracentrifuge. Following ultracentrifugation, purified plasmid DNA was dialyzed against a buffer which consisted of 10.0 mM tris, 15.0 mM NaCl, and 2.0 mM EDTA in water. pH was 8.0.

Plasmid DNA was subjected to electrophoresis. A Tris-borate gel buffer was used. It consisted of 10.8 g/l of Tris, 5.5 g/l of borate, and 4.0 ml. of a 0.5 M Na2EDTA solution (pH 8.0). Large gels were run on the BRL Horizontal Gel Electrophoresis System Model H3 in 0.7% (w/v) agarose gels at 80 volts for 3 hours. Mini gels were performed on the Hoefer Scientific HE 33 "Minnie" Horizontal Submarine Unit in 1.0% (w/v) agarose gels at 140 volts for 45 minutes. The Heath Zenith Regulated H.V. Power Supply Model SP-2717A was used with both units. The tracking dye was 50% glycerol, 0.07% bromophenol blue, and 50.0 mM of EDTA in water.

Gels were stained with ethidium bromide, 0.1 ug/ml in Tris-borate buffer, in the dark for one half hour.

All gels were photographed using an Ultra Violet Products Chromato-Vue transilluminator Model TM-36 with a Polaroid MP-4 land Camera 44–01 equipped with a red filter. Mini-survey lysis (HOL II), a small, quick assay, and the multiplate procedures were employed for plasmid extraction. HOL II is used in association with gel electrophoresis for rapid initial examination of bacteria to determine the presence or absence of plasmids. The multiplate Hansen and Olsen method (HO) is used when large amounts of plasmid DNA are to be extracted.

The Hansen and Olsen multiplate procedure, in association with cesium-chloride equilibrium density gradient centrifugation, was employed in isolating plasmids. The results were consistent and reproducible. The procedure was modified slightly to accomodate the nature of the microorganism. The isolate was resistant to lysing possibly due to the fact that it originated from such an extreme environment. Therefore, the lysis step was extended from five to sixty minutes to provide for more complete lysing of the cell suspension. Also, mutanolysin, instead of lysozyme, was used as the lysing agent.

The results using the HO procedure showed that *Klebsiella oxytoca* strain SAL-18A contained a large plasmid comparable in size to the larger plasmid of *Pseudomonas cepacia* strain SS3. Previously, three large plasmids were found in strain SS3 using the Hansen and Olsen procedure and it was demonstrated that the chloro aromatic degradative ability of strain SS3 was transmissible via these plasmids. These plasmids were identified as pRo 4.7, pRo 31 and pRo 54 in U.S. Pat. No. 4,447,570.

The fact that this isolate possessed plasmids suggested that the plasmids coded for the degradation of complex organic compounds. It was obtained from leachate from a landfill site which had been used for the disposal of chlorinated organic wastes. Plasmids have been shown to code for the dissimilation of complex organic compounds to simple organic acids which can be used in the central pathways of the microorganism. They can spread among indigenous populations via recombination, conjugation, or transformation thus serving the evolutionary process via the conferring of genetic diversity. They may have evolved as a survival mechamism for microorganisms in extreme environments. Under conditions of high localized concentrations of toxic substances, as existed at the landfill, plasmid encoded functions are capable of detoxifying the environment. The plasmids in the present microorganism may have evolved for this purpose.

Although various embodiments of this invention have been shown and described in the specification, this invention is intended to be construed liberally and not limited by any specific embodiments as will be readily appreciated by those skilled in the art. It is to be understood, therefore, that the appended claims are intended to cover all modifications and variations which are within the spirit and scope of the present invention.

What is claimed is:

1. A biologically pure culture of the facultatively anaerobic microorganism selected from the group consisting of *Klebsiella oxytoca* strain SAL-18A and mutations thereof, said microorganism being further identified by accession number IVI-10113, said microorganism being capable of degrading haloaromatic compounds in a solid medium.

2. A process for the microbial degradation of toxic halogenated organic chemical waste into less toxic materials, which comprises applying the locus of said halogenated organic chemical waste a biologically pure culture of the microorganism selected from the group consisting of *Klebsiella oxytoca* strain SAL-18A and mutations thereof, said microorganism being further identified by accession number IVI-10113, and monitoring the removal of contaminants from the waste locus.

3. The process of claim 2 wherein the locus of the waste to be degraded is soil containing halogenated organic chemical waste, the soil being cultivated in the presence or absence of oxygen or air with the microorganism and combined with a nutrient.

4. The process of claim 3 wherein the locus to be degraded is a landfill.

5. The process of claim 3 wherein the locus to be degraded is a leachate removed from the landfill.

6. The process of claim 2 wherein the halogenated organic chemicals are predominantly chlorinated aromatic chemicals.

7. The process of claim 6 wherein the metabolic pathway for degradation includes one or more chloro benzoic acid compounds.

8. A process for biologically treating chemical process wastewater and chemical waste landfill leachate in a sequencing batch reactor system to degrade the recalcitrant organic compounds contained therein comprising the steps of:
  (a) establishing an activated sludge in the sequencing batch reactor containing a liquid medium having both recalcitrant and non-recalcitrant organic compounds, said activated sludge being capable of metabolizing the non-recalcitrant components of the wastewater or leachate,
  (b) augmenting the activated sludge with a biologically pure culture of the microorganism selected from the group consisting of *Klebsiella oxytoca* strain SAL-18A and mutations thereof, said microorganism being capable of metabolizing the recalcitrant organic compounds and being further identified by accession number IVI-10113,
  (c) forming a stable biomass in the reactor capable of biodegrading the recalcitrant and non-recalcitrant components of the chemical process wastewater or leachate, and
  (d) disposing of the waste effluent and waste sludge produced in the reactor.

9. The process of claim 8 wherein the recalcitrant compounds are chlorinated aromatic compounds.

10. The process of claim 9 wherein the chlorinated aromatic compounds are chlorobenzoic acids.

* * * * *